(12) United States Patent
Madabhushi et al.

(10) Patent No.: US 10,235,755 B2
(45) Date of Patent: Mar. 19, 2019

(54) HIGH-THROUGHPUT ADAPTIVE SAMPLING FOR WHOLE-SLIDE HISTOPATHOLOGY IMAGE ANALYSIS

(71) Applicant: Case Western Reserve University, Cleveland, OH (US)

(72) Inventors: Anant Madabhushi, Shaker Heights, OH (US); Angel Alfonso Cruz Roa, Villavicencio (CO); Fabio Gonzalez, Bogota (CO)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 16/023,361

(22) Filed: Jun. 29, 2018

(65) Prior Publication Data

US 2018/0322631 A1 Nov. 8, 2018

Related U.S. Application Data

(62) Division of application No. 15/282,233, filed on Sep. 30, 2016, now Pat. No. 10,049,450.

(Continued)

(51) Int. Cl.
*G06K 9/00* (2006.01)
*G06T 7/00* (2017.01)
(Continued)

(52) U.S. Cl.
CPC ........ *G06T 7/0012* (2013.01); *A61B 10/0041* (2013.01); *G06F 19/00* (2013.01);
(Continued)

(58) Field of Classification Search
None
See application file for complete search history.

(56) References Cited

U.S. PATENT DOCUMENTS 9,842,391 B2 12/2017 Tunstall et al.
2016/0070949 A1 3/2016 Tunstall et al.

OTHER PUBLICATIONS

Ciresan, et al. "Mitosis Detection in Breast Cancer Histology Images with Deep Neural Networks." MICCAI 2013, Part II, LNCS 8150, pp. 411-418, published 2013.

(Continued)

*Primary Examiner* — Soo Jin Park
(74) *Attorney, Agent, or Firm* — Eschweiler & Potashnik, LLC

(57) ABSTRACT

Methods, apparatus, and other embodiments associated with classifying a region of tissue represented in a digitized whole slide image (WSI) using iterative gradient-based quasi-Monte Carlo (QMC) sampling. One example apparatus includes an image acquisition circuit that acquires a WSI of a region of tissue demonstrating cancerous pathology, an adaptive sampling circuit that selects a subset of tiles from the WSI using an iterative QMC Sobol sequence sampling approach, an invasiveness circuit that determines a probability of a presence of invasive pathology in a member of the subset of tiles, a probability map circuit that generates an invasiveness probability map based on the probability, a probability gradient circuit that generates a gradient image based on the invasiveness probability map, and a classification circuit that classifies the region of tissue based on the probability map. A prognosis or treatment plan may be provided based on the classification of the WSI.

31 Claims, 8 Drawing Sheets

Related U.S. Application Data

(60) Provisional application No. 62/262,756, filed on Dec. 3, 2015.

(51) Int. Cl.

| | | |
|---|---|---|
| *G16H 30/20* | (2018.01) | |
| *G06F 19/00* | (2018.01) | |
| *G16H 50/20* | (2018.01) | |
| *A61B 10/00* | (2006.01) | |
| *G06K 9/46* | (2006.01) | |
| *G06K 9/62* | (2006.01) | |
| *G06N 7/00* | (2006.01) | |

(52) U.S. Cl.
CPC ......... *G06K 9/4604* (2013.01); *G06K 9/4628* (2013.01); *G06K 9/4642* (2013.01); *G06K 9/627* (2013.01); *G06K 9/6269* (2013.01); *G06K 9/6277* (2013.01); *G06N 7/005* (2013.01); *G16H 30/20* (2018.01); *G16H 50/20* (2018.01); *G06K 2209/051* (2013.01); *G06T 2207/10024* (2013.01); *G06T 2207/10056* (2013.01); *G06T 2207/20021* (2013.01); *G06T 2207/20084* (2013.01); *G06T 2207/30024* (2013.01); *G06T 2207/30096* (2013.01)

(56) References Cited

OTHER PUBLICATIONS

Malon, et al. "Classification of Mitotic Figures with Convolutional Neural Networks and Seeded Blob Features." J Pathol Inform 2013;4:9, published May 30, 2013.

He, et al. Histology Image Analysis for Carcinoma Detection and Grading."Computer Methods and Programs in Biomedicine." 107 (2012) 538-556, published in 2012.

Daniel, et al. "Standardizing the Use of Whole Slide Images in Digital Pathology." Computerized Medical Imaging and Graphics. 35 (2011) 496-505, published in 2012.

Kothari, et al. "Pathology Imaging Informatics for Quantitative Analysis of Whole-Slide Images." J Am Med Inform Assoc 2013; 20: 1099-1108, published Aug. 19, 2013.

Notice of Allowance dated Apr. 13, 2018 for U.S. Appl. No. 15/282,233.

HIGH-THROUGHPUT ADAPTIVE SAMPLING FOR WHOLE-SLIDE HISTOPATHOLOGY IMAGE ANALYSIS

CROSS REFERENCE TO RELATED APPLICATIONS

This Application is a Divisional of U.S. application Ser. No. 15/282,233 filed on Sep. 30, 2016, which claims priority to U.S. Provisional Application No. 62/262,756 filed on Dec. 3, 2015. The contents of the above-referenced applications are hereby incorporated by reference in their entirety.

FEDERAL FUNDING NOTICE

The invention was made with government support under grants R01CA136535-01, R01CA140772-01, R21CA167811-01, R21CA179327-01, R21CA195152-01, and R01 DK098503-02, awarded by the National Institutes of Health. Also grants W81XWH-13-1-0418, and W81XWH-14-1-0323, awarded by the Department of Defense. The government has certain rights in the invention.

BACKGROUND

Precise detection of invasive regions of cancer on a whole-slide image (WSI) is a critical first step in enabling subsequent further interrogation of tumor differentiation using standard grading schemes. WSIs used in histopathology are typically large. For example, a typical WSI may have a spatial resolution of 80,000 pixels by 80,000 pixels and require 20 GB to store. Furthermore, digital slide repositories, such as the Cancer Genome Atlas (TCGA) may host images acquired from thousands of cancer studies performed by different institutions, amounting to petabytes of data that may be analyzed. This high volume of data requires high throughput computational image analysis techniques to effectively utilize the data in clinical applications.

Representation and deep learning approaches may be used for interpretation and analysis of images. Representation and deep learning approaches may be used instead of other computer vision approaches for tasks including object detection, object recognition, and image annotation. Deep representation learning refers to a family of machine learning methods that attempt to learn multiple levels of representation to model complex relations among data. Deep representation learning methods attempt to discover more abstract features via higher levels of representation. Convolutional neural networks (CNN) are a type of deep representation learning method that may be used for image analysis. CNNs are multilayer neural networks that combine different types of layers (e.g. convolutional, pooling, classification) that are trained in a supervised manner for image analysis and classification tasks.

Conventional approaches employing CNNs for image classification and object detection have focused on very small images. Some conventional approaches have applied CNNs to histopathology image analysis, including analysis of WSIs. However, conventional approaches to image analysis using CNNs have limited their analysis to small regions of interest (ROI) within the larger WSI. The overall size of a CNN depends on the size of the input image. For example, a CNN with an input image having dimensions of 200 pixels by 200 pixels and 250 feature maps in the first convolutional layer would involve ten million hidden units. In contrast, the same CNN architecture with an input red-green blue (RGB) color model image of 80,000 pixels by 80,000 pixels (e.g. a typical digitized WSI) would require approximately 4.8 trillion hidden units, which exceeds the computational capabilities of contemporary high performance computing clusters by several orders of magnitude. Consequently, the direct application of conventional CNN approaches to object detection or pixel-level classification in WSIs is not tenable in clinically relevant time-frames.

Breast cancer (BCa) is the most common type of cancer in women and the second leading cause of death in developed countries. Invasive BCa refers to those breast cancers that have spread from the original site and which tend to have poorer prognosis than less invasive BCa. Precise invasive tumor delineation on a pathology slide is typically the first step for subsequent interrogation of tumor differentiation. Conventional approaches to BCa grading have first required a definition of the target ROI on a WSI by an expert human pathologist. Thus, conventional approaches are limited by the availability of expert human pathologists, and by inter-reviewer subjectivity.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
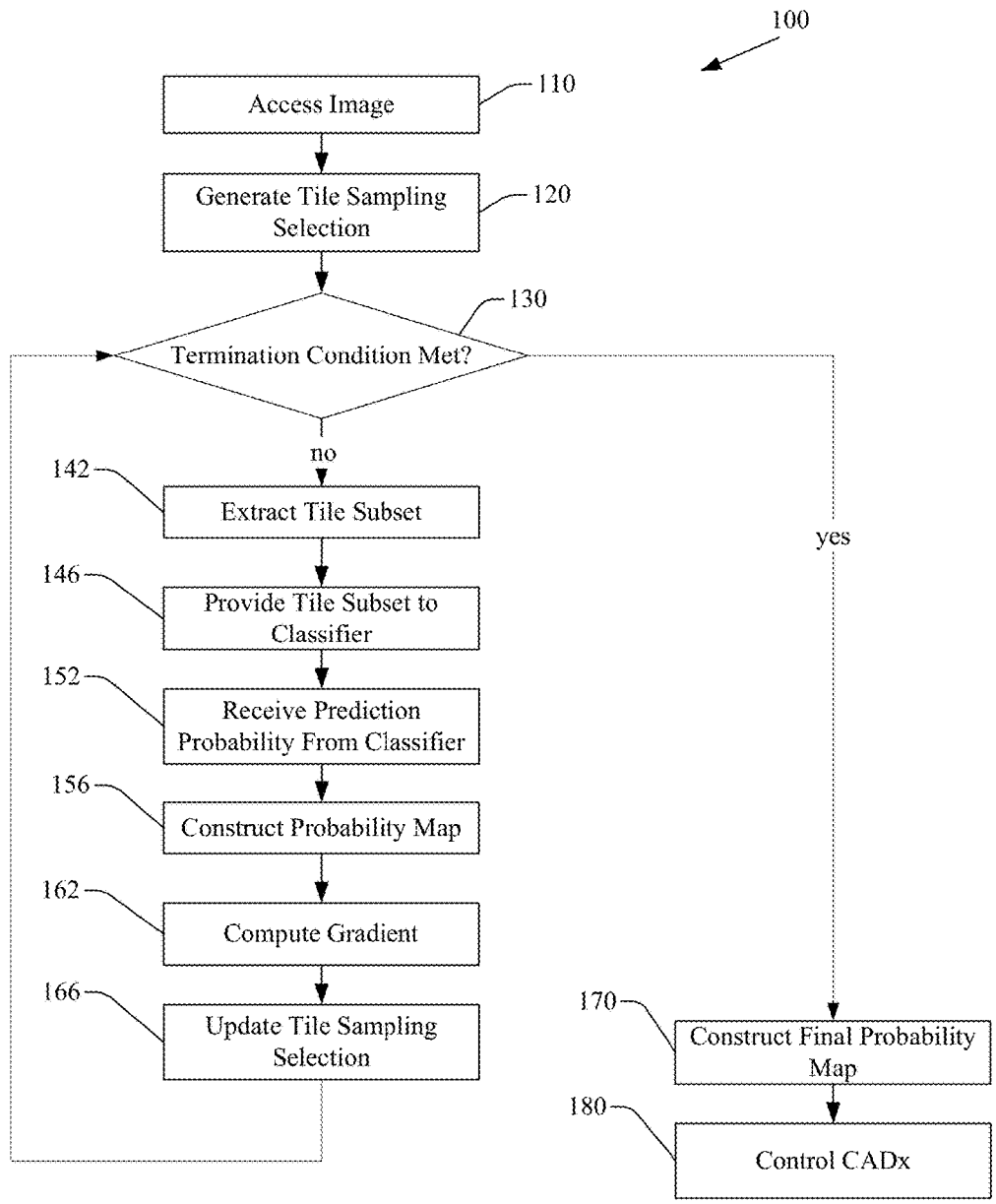
FIG. 1 illustrates an example method for detecting cancerous pathology in a region of tissue.

Conventional approaches to histopathology image analysis may focus on identification of image features in conjunction with a machine learning classifier to predict the presence or severity of disease from surgical or biopsy tissue specimens. These approaches that involve feature extraction from digital pathology images are based on hand-crafted feature design. Hand-crafted features aim to capture different tissue morphologic and spatial properties, including nuclear shape, nuclear architecture, color intensity, and tissue texture. Hand-crafted features are sensitive to staining and scanning artifacts, and may be approximations based on mathematical and statistical formulations of visual content. Consequently, hand-crafted features may not capture all the relevant characteristics and complex relationships embedded within disease patterns manifested on histopathology images.

Representation learning aims to automatically learn the transformation of data that facilitates high-level prediction and classification tasks using one level or multiple levels of representation. Compared to hand-crafted features, representation learning approaches attempt to learn the most appropriate representation directly from the data. While some representation learning approaches tend to be domain agnostic, in that they do not specifically invoke visual features that represent the domain, they are focused on identifying image features geared towards maximizing high-level classification tasks in pattern recognition. While some approaches to representation learning in histopathology image analysis using CNNs have employed unsupervised learning, most employ supervised learning. Additionally, conventional approaches to histopathology image analysis of WSIs are limited to manually selected ROIs, small images, or to use at low magnification levels.

Conventional approaches to image analysis of WSIs for use in characterizing BCa invasiveness have thus been limited to small ROIs within larger WSIs. Furthermore, hand-crafted features tend to be very specific to particular domains or data sources, and are not seamlessly generalizable to different tasks or applications. Additionally, conventional approaches have been evaluated on relatively small cohorts of case studies, typically originating from a single institution. Thus, conventional approaches may not actually be useful in routine clinical practice.

Example methods and apparatus facilitate more accurate and faster analysis of WSI images than conventional approaches by using high-throughput gradient-based adaptive sampling for whole-slide histopathology image analysis. Example methods and apparatus employ efficient adaptive sampling based on a probability gradient and quasi-Monte Carlo sampling, and further employ a representation learning classifier based on convolutional neural networks. Example methods and apparatus access a WSI and extract tiles from the WSI using random sampling. Example methods and apparatus apply a CNN classifier to an extracted tile, and produce a prediction associated with the tile. Example methods and apparatus use the prediction associated with the tile to build an interpolated probability map. Example methods and apparatus use the interpolated probability map to identify regions in the WSI that have a high uncertainty with respect to tissue type or class. Example methods and apparatus determine which regions are to receive denser sampling by choosing high gradient magnitudes that are associated with target class borders. Newly sampled tiles are selected based on a gradient magnitude, and are used to produce an improved probability map estimation. Example methods and apparatus may then iterate the steps or actions described herein to produce a final classification map. In one embodiment, example methods and apparatus analyze a WSI of a region of tissue demonstrating BCa pathology, and produce a final invasive BCa probability map. Example methods and apparatus thus improve on conventional approaches by facilitating more accurate and more reproducible detection of invasive BCa on new or unseen WSIs, and by generalizing to images acquired from different data sources and domains. Example methods and apparatus further improve on conventional approaches by being an order of magnitude more efficient than conventional approaches that use naïve implementations of CNNs, by using high-throughput adaptive sampling that facilitates the analysis of WSIs in a clinically relevant timeframe.

Example methods and apparatus may train and test a classifier. Example methods and apparatus may train a CNN classifier using training exemplars generated on digitized WSIs obtained from a training cohort. The training cohort may be acquired from one, or from more than one, institution. For example, a human pathologist may manually delineate and classify invasive BCa tissue and non-invasive BCa tissue in digital WSIs of tissue demonstrating BCa for a testing set. A training phase of the CNN may use as input a tile-based dataset obtained by applying a regular sampling of WSIs from the training cohort. The training exemplars may be annotated by an expert pathologist. Example methods and apparatus may extract tiles of a fixed size from annotated invasive tissue regions and annotated non-invasive tissue regions.

Example methods and apparatus may classify a region of tissue as non-invasive BCa or invasive BCa, including estrogen receptor-positive (ER+) BCa. Other classifications may be employed. For example, methods and apparatus disclosed herein may classify a region of tissue demonstrating prostate cancer, oral cancer, or other type of cancer characterized by invasive tissue, as invasive or non-invasive.

Example methods and apparatus may train and test a classifier using data sets acquired from different institutions, or acquired with different scanners. For example, in one embodiment, a CNN classifier was trained on a data cohort acquired from the Hospital of the University of Pennsylvania comprising WSIs acquired from 239 different patients using an Aperio scanner. In another embodiment, the CNN classifier was trained using a data cohort acquired from the Hospital of the University of Pennsylvania and University Hospitals Case Medical Center/Case Western Reserve University comprising WSIs acquired from 349 different patients using Aperio scanners and Ventana scanners. Other sizes of training sets, sizes of testing sets, or scanners may be employed.

In one embodiment, example methods and apparatus employ adaptive gradient-based sampling to iteratively refine an initial coarse estimation of an invasive BCa probability map. Example methods and apparatus may receive as inputs a WSI X, a termination condition T, which may be a maximum number of iterations or other termination condition, and a number N of sample points per iteration. The WSI comprises a set of tiles. Example methods and apparatus perform a tile sampling process that generates a subset of tiles from the set of tiles. The subset of tiles contains N tiles. A member of the subset of tiles is classified using a CNN-trained model to obtain a probability of the presence of invasive BCa at the location occupied by the member of the subset of tiles. Example methods and apparatus interpolate the probabilities calculated for the subset of tiles and generate a probability map P for the WSI. To determine regions in the WSI that have a higher uncertainty as to whether the region is invasive or non-invasive, a gradient G of the probability map P is calculated. The gradient G is used to prioritize the sampling selection of new tiles for the next iteration. Tiles having a higher uncertainty, as represented by a higher gradient magnitude, will be more likely to be selected in the next iteration than tiles with a lower uncertainty. Example methods and apparatus may continue until the termination condition T is met.

Example methods and apparatus may train a CNN classifier. A regular sampling may be performed on an RGB color model WSI selected from a member of a training set of WSIs. Tiles corresponding to tissue regions in the WSI may be selected, while tiles corresponding to background regions may be ignored. A tile may be considered to be a positive sample including invasive BCa if a threshold proportion or more than the threshold proportion of the tile area overlaps with a region annotated by an expert pathologist as being invasive. A tile may be considered to be a negative sample if less than a threshold proportion of the tile area overlaps with the region annotated as being invasive. Selected tiles are converted from RGB color space to YUV color space and are normalized to a mean of zero and a variance of one. Color space transformation and normalization facilitates decolorization and accentuation of differences between input image tiles, independent of color variability. Example methods and apparatus thus facilitate the acceleration of the gradient-based learning process during the training of the classifier.

Example methods and apparatus may employ a two-layer CNN classifier. In one embodiment, the two-layer CNN architecture includes a first layer comprising a 256 unit or neuron convolutional layer and a 256 unit or neuron pooling layer. The two-layer architecture may also include a fully connected layer of 256 units or neurons. The two-layer architecture may be identified as a (CS256-FC256) architecture. The two-layer architecture further includes a classification layer. The classification layer may include a softmax classifier. The classification layer may have two outputs that classify the input image as, for example, invasive or non-invasive. The convolution layer applies a two-dimensional (2D) convolution of the input image with a kernel of 8 pixels by 8 pixels to produce a feature map. The pooling layer, which may also be referred to as a subsampling layer, applies a spatial L2-pooling function without overlapping, employing a pooling kernel of 2 pixels by 2 pixels for a feature map obtained from the convolution layer. The L2-pooling function allows the classifier to learn invariant features. The output of the pooling layer is fed to the fully-connected layer followed by the final classification layer. Example methods and apparatus may use tiles sampled from both invasive tissue regions and non-invasive tissue regions as input to the CNN. In other embodiments, other CNN architectures may be employed, including (CS16-CS32-FC-128) or (CS16-CS16-CS16-FC128) architectures.

Example methods and apparatus may further train the CNN classifier. In one embodiment, the CNN classifier is trained using a stochastic gradient descent approach to minimize a softmax loss function. An example softmax loss function suitable for use by example embodiments is:

$$L(W) = -\frac{1}{M}\left[\sum_{i=1}^{m}\sum_{j=1}^{C}1\{y^{(i)} = c\}\log\frac{e^{w_c s^{(i)}}}{\sum_{l=1}^{C} e^{w_l s^{(i)}}}\right] + \frac{\lambda}{2}\|W\|_F^2 \quad \text{(Eq. 1)}$$

where m is the number of training samples, C is the number of classes, $W \in \mathbb{R}^{C \times n}$ are the weights of the network in the last layer with $w_c$ as the vector associated with a class c, $s^{(i)} = f(x^{(i)})$ is the feature vector for sample i, $x^{(i)}$ is the output of the fully-connected layer, $y^{(i)} \in \mathbb{N}$ is the label associated with a sample I, and $\lambda$ is the regularization parameter. 1{statement} function outputs 1 if statement is true, or outputs 0 otherwise. The CNN training process includes searching for a weight vector W that minimizes the loss function expressed by equation 1. The CNN training process may be implemented using machine learning frameworks, including Torch 7, or other machine learning frameworks.

To predict the likelihood of individual tiles representing invasive disease, conventional approaches repeatedly apply a classifier to each tile in a WSI. For a standard digitized WSI with dimensions of 80,000 pixels by 80,000 pixels, a conventional tile sampling approach involving tile sizes of 101 pixels by 101 pixels results in over $6.39 \times 10^9$ predictions, which is computationally infeasible in clinically relevant time frames. For example, using a CNN and dense regular sampling, which is a case of regular sampling in which the step size is one pixel, conventional approaches may take 22 hours or more to analyze a single WSI. Example methods and apparatus improve on conventional approaches by making a prediction of invasiveness on members of a sample of patches selected from the WSI, and then by extrapolating from these predictions to generate a prediction for non-sampled regions of the WSI. Example methods and apparatus employ an adaptive sampling approach that performs an iterative, gradient guided sampling focusing on areas of the image that demonstrate higher uncertainty.

Example methods and apparatus select a set of tiles from a WSI which are then used to generate a probability map over the WSI. The tiles may be selected by random sampling. Conventional approaches may use dense regular sampling. Regular sampling involves sampling tiles at equally spaced intervals on a regular grid. For instance, given a WSI of K×K size and using tiles of size k×k, the step size sin both the X and Y directions is 1≤s≤k. The extreme case involves using a step size s=1, which results in an expected number of samples of $(K-k)^2$. This case corresponds to a dense sampling of the WSI.

Regular sampling is deterministic. Example methods and apparatus may employ random sampling. Random sampling involves selecting tiles using random co-ordinates generated from a particular probability distribution. Without a priori knowledge of the image content, a uniform probability distribution may be used as a random sampling approach. Uniform random sampling may over-sample tiles in some regions of the WSI while leaving other regions under represented. Thus, uniform random sampling may not be an optimal sampling approach since predictions on over-represented regions tend to be redundant, thereby wasting time and computational resources.

Example methods and apparatus may employ quasi-Monte Carlo (QMC) sampling. QMC sampling facilitates a more efficient sampling strategy and a more regular spatial exploration than regular sampling. QMC sampling employs a deterministic or pseudo-random sequence that has low discrepancy. Discrepancy is herein used to refer to a measure of the uniformity of a distribution of finite point sets. Low discrepancy is an advantage for QMC compared to conventional approaches, including Monte Carlo methods based on random sampling, because QMC does not result in clumping or the accumulation of samples in a small area. Thus, example methods and apparatus improve on conventional approaches. Example methods and apparatus may employ a Sobol sequence or a Halton sequence when implementing QMC sampling. Example methods and apparatus thus further improve on conventional approaches by facilitating the incremental addition of sampling points without discarding sampling points already previously generated.

Example methods and apparatus generate an invasiveness probability map estimation. In one embodiment, sampled tiles are provided to a CNN classifier to determine the probability of the presence of invasive or non-invasive pathology in a tile. Example methods and apparatus may determine the probability of the presence of non-invasive or invasive BCa, other types of cancer, or other pathologies.

Example methods and apparatus apply cubic interpolation to extend the probability or estimation to other pixels in the WSI. Example methods and apparatus generate an invasiveness probability map P during an iteration in which a first set of sample tiles are provided to the CNN classifier, which provides a first probability determination, and in which a first probability map is generated.

Example methods and apparatus may calculate a gradient image $\nabla P$ based on the probability map P. The gradient image $\nabla P$ facilitates determining directional changes in the probability map P. In one embodiment, the gradient image $\nabla P$ may be expressed as $$\nabla P = \frac{\partial P}{\partial x}\hat{x} + \frac{\partial P}{\partial y}\hat{y} \quad \text{(Eq. 2)}$$

where $$\frac{\partial P}{\partial x}$$

represents the gradient in the X direction, and $$\frac{\partial P}{\partial y}$$

represents the gradient in the Y direction.

Example methods may compute a gradient magnitude image $|\nabla P|$ to facilitate identifying regions with variations among tissue types in the probability map P. The variations may be high or low variations among tissue types, including, for example, invasive or non-invasive BCa. In one embodiment, the gradient magnitude image $|\nabla P|$ may be expressed as $$|\nabla P| = \sqrt{\left(\frac{\partial P}{\partial x}\right)^2 + \left(\frac{\partial P}{\partial y}\right)^2} \quad \text{(Eq. 3)}$$

High values in the gradient magnitude image $|\nabla P|$ (e.g. strong changes) correspond to a heterogeneous spatial distribution of both invasive and non-invasive tissue types along, for example, tumor boundaries. Low values in the gradient magnitude image $|\nabla P|$ (e.g. soft changes) correspond to a homogeneous distribution of either invasive or non-invasive tissue types. Thus, the magnitude $|\nabla P|$ has low values if the local spatial regions of P have similar values. In contrast, the magnitude $|\nabla P|$ is high if the local spatial regions of P have less similar probability values.

Example methods and apparatus improve on conventional approaches by employing the probability gradient to facilitate a more intelligent, efficient, and effective spatial sampling of points. Example methods and apparatus may more densely sample regions with higher $|\nabla P|$ values within the gradient map, which represent transitional areas from one tissue type to another. Example methods and apparatus may also extract fewer samples from homogenous regions that have lower $|\nabla P|$ values, which may represent a region of a single tissue type. In one embodiment, example methods and apparatus may generate 2N samples using random or QMC sampling approaches. In this embodiment, the 2N samples may be ranked according to the magnitude of $|\nabla P|$. Example methods and apparatus may then select the top N samples to provide samples for the next iteration. In another embodiment, other techniques other than ranking may be employed to select those samples having higher $|\nabla P|$ values from the 2N samples, including sorting methods.

Example methods and apparatus thus improve on conventional methods by faster and more accurately classifying a region of tissue as invasive or non-invasive. Example methods and apparatus classify a region of tissue represented in an 80,000 pixel by 80,000 pixel digitized WSI as containing invasive BCa tissue or non-invasive BCa tissue with an accuracy of at least 0.9018 area under the curve (AUC) in approximately 30 seconds when using iterative gradient-based QMC sampling with a Halton sequence and a (CS256-FC256) architecture two-layer CNN. In contrast, conventional approaches analyzing the same WSI using the same CNN with dense regular sampling achieve similar accuracies but take over 22 hours. Conventional approaches analyzing the same WSI using the same CNN with regular grid sampling achieve inaccurate coarse and imprecise classifications in similar timeframes. Example methods and apparatus thus facilitate a significant, measurable increase in speed and accuracy compared to conventional approaches.

By increasing the speed and accuracy with which regions of tissue demonstrating invasive BCa or non-invasive BCa are classified, example methods and apparatus produce the concrete, real-world technical effect of reducing the time required to evaluate medical imagery while increasing the accuracy of the evaluation. Additionally, example apparatus and methods increase the probability that at-risk patients receive timely treatment tailored to the particular pathology they exhibit. Example methods and apparatus may also reduce the number of invasive procedures needed to accurately characterize a region of tissue. The additional technical effect of reducing the expenditure of resources and time on patients who are less likely to suffer recurrence or disease progression is also achieved. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a circuit or logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 illustrates an example computerized method 100 for detecting cancerous pathology in a region of tissue. Method 100 includes, at 110, accessing an image of a region of tissue demonstrating cancerous pathology. The image comprises a set of tiles. In one embodiment, the image of the region of tissue is a digitized whole slide image (WSI) of a region of tissue demonstrating estrogen receptor-positive (ER+) BCa. In one embodiment, the WSI is a red-green-blue (RGB) color model WSI, with dimensions of 80 000 pixels by 80 000 pixels. In one embodiment, a member of the set of tiles may have dimensions of 101 pixels by 101 pixels. In another embodiment, the member of the set of tiles may have other, different dimensions, the WSI may be a different color model WSI, or the WSI may have other, different dimensions. In another embodiment, the image may be a WSI of a region of tissue demonstrating other cancerous pathologies, including prostate cancer, oral cancer, lung cancer, or esophageal cancer. Accessing the image may also include accessing another type of medical image, or accessing a medical image of a region of tissue demonstrating a different, non-cancerous pathology. Accessing the image may include retrieving electronic data from a computer memory, receiving a computer file over a computer network, or other computer or electronic based action.

Method 100 also includes, at 120, generating a tile sampling selection. The tile sampling selection defines a sampling subset of the set of tiles. The number of tiles in the sampling subset is N, where N is less than the number of tiles in the set of tiles, N being an integer. In one embodiment, N=100. In another embodiment, the number of tiles in the sampling subset may be another, different number. Generating the tile sampling selection includes selecting the sampling subset of the set of tiles using a regular sampling approach, a uniform random sampling approach, or a quasi-Monte Carlo (QMC) sampling approach. In one embodiment, the QMC approach employs a deterministic sequence. The deterministic sequence used by the QMC approach has a low discrepancy. The deterministic sequence measures a uniformity of a distribution of finite point sets. In one embodiment, the deterministic sequence is a Sobol sequence or a Halton sequence.

Method 100 also includes, at 130, determining if a termination condition has been met. In one embodiment, the termination condition is a number of iterations. For example, the termination condition may be twenty iterations. In another embodiment, the termination condition may be a steady state condition, or a processing time limit. In another embodiment, other termination conditions may be employed. For example, the termination condition may be a minimum epsilon value for the average magnitude gradient. In another embodiment, the termination condition may be a minimum approximation error between the current probability map and a previous probability map. The minimum approximation error may be based on a mean squared error (MSE). The termination condition may be user controlled.

Upon determining that the termination condition has not been met, method 100 proceeds to block 142. Method 100 includes, at 142, extracting the sampling subset from the image based on the tile sampling selection. Extracting the sampling subset may include, for example, accessing the N tiles defined by the tile sampling selection from the set of tiles.

Method 100 also includes, at 146, providing the sampling subset to an automated classifier. In one embodiment, the automated classifier is a 2-layer convolutional neural network (CNN). The CNN may include a first layer comprising a 256 unit convolutional layer and 256 unit pooling layer. The convolutional layer generates a feature map by applying a 2D convolution of an input image with an 8 pixel by 8 pixel kernel. The pooling layer applies a spatial L2 pooling function without overlapping to the feature map. The pooling layer employs a 2 pixel by 2 pixel pooling kernel for the feature map generated by the convolutional layer. The CNN may also include a second layer comprising a 256 unit fully-connected layer. The CNN may further include a classification layer. The classification layer may be a softmax classifier. The classification layer produces a first output or a second output. The first output is activated by a logistic regression function. The second output is also activated by the logistic regression function. The first output may indicate that input to the classifier represents invasive tissue, while the second output may indicate that input to the classifier represents non-invasive tissue.

Method 100 also includes, at 152, receiving, from the automated classifier, a prediction probability. The prediction probability is based, at least in part, on the sampling subset. The prediction probability indicates the probability of invasive pathology at a location in the WSI occupied by a tile. In one embodiment, the prediction probability may be within, for instance, a range of 1 for invasive tissue, to 0 for non-invasive tissue. In one embodiment, a prediction probability in the range (0.4, 0.6) indicates a threshold uncertainty as to whether the tissue at the location occupied by the tile is invasive or non-invasive. Other threshold uncertainty values may be employed. Regions of uncertainty may be candidates for sampling in further iterations.

Method 100 also includes, at 156, constructing a probability map of the region of tissue based on the prediction probability and the sampling subset. In one embodiment, constructing the probability map includes cubically interpolating the prediction probability to a plurality of pixels in the WSI. For example, in one embodiment, the automated classifier may return probabilities associated with members of the sampling subset. Example methods and apparatus may extend the estimation represented by the returned probabilities to other regions of the WSI using cubic interpolation. In another embodiment, example methods and apparatus may extend the estimation using other techniques.

Method 100 also includes, at 162, computing a gradient of the probability map. In one embodiment, computing the gradient of the probability map includes calculating a gradient image. The gradient image is based on an X direction gradient and a Y direction gradient. The X direction gradient represents a directional change of the probability map in the X direction. The Y direction gradient represents a directional change of the probability map in the Y direction. Computing the gradient of the probability map further includes computing a gradient magnitude image. The gradient magnitude image is based, at least in part, on the gradient image, or the X direction gradient and the Y direction gradient.

Figure 4:
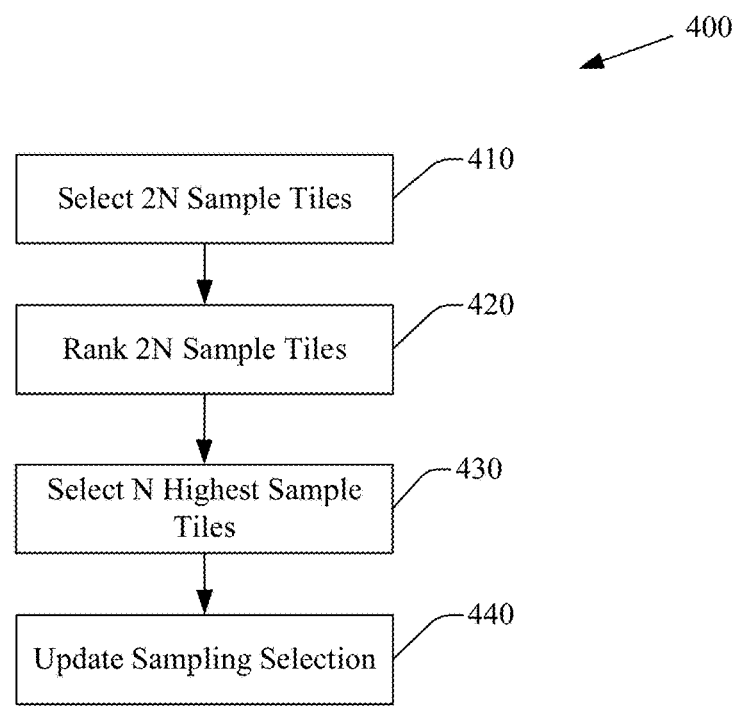
FIG. 4 illustrates an example method for updating a sampling selection of WSI tiles.

Method 100 also includes, at 166, updating the tile sampling selection based on the gradient of the probability map or the gradient image. Updating the tile sampling selection includes selecting 2N sample tiles from the set of tiles, where 2N is an integer. The 2N sample tiles may be selected using a quasi-Monte Carlo sampling approach or a random sampling approach. Updating the tile sampling selection further includes generating an updated sampling selection by determining the N tiles that have the highest gradient magnitude from among the 2N sample tiles. FIG. 4 illustrates one example method 400 for determining the N tiles that have the highest gradient magnitude from among the 2N sample tiles.

Method 400 includes, at 410, selecting a set of 2N sample tiles from the set of tiles. The set of 2N sample tiles may be selected using random sampling or QMC sampling. Method 400 also includes, at 420, generating a ranked set of sample tiles by ranking the 2N sample tiles according to a gradient magnitude associated with a member of the set of 2N sample tiles. The ranked set may be ranked based, at least in part, on the gradient magnitude image. Method 400 also includes, at 430, selecting the N highest ranked tiles from the ranked set of sample tiles. Method 400 also includes, at 440, updating the sampling selection with the N highest ranked tiles. In another embodiment, other approaches to determining the N tiles that have the highest gradient magnitude from the 2N sample tiles may be employed. In another embodiment, other numbers of sample tiles or ratios of highest ranked tiles to sample tiles may be selected.

Upon determining that the termination condition has been met, method 100 proceeds to block 170. Method 100 includes, at 170, constructing a final probability map based, at least in part, on the probability map. The final probability map may be provided to a computer aided diagnosis (CADx) system, or may be displayed on a computer monitor, a tablet computer, a smartphone, or other display. Displaying the final probability map may also include printing the final probability map.

In one embodiment, method 100 also includes, at 180, controlling a CADx system to generate a classification of the region of tissue. The classification of the region of tissue may be based, at least in part, on the final probability map. The classification facilitates the timely, efficient, and accurate application of treatments for invasive pathologies, including BCa.

Example methods and apparatus facilitate more accurate characterization of invasive pathology found in WSI images than conventional approaches. Example methods and apparatus thus improve on conventional methods by characterizing invasive pathology faster and with greater accuracy and with less subjective variability than conventional methods. Example methods and apparatus therefore facilitate more judicious application of biopsies and surgical resection to patients demonstrating invasive pathologies, including BCa. Example methods and apparatus therefore facilitate more efficient and accurate targeting and application of BCa treatment.

Using a more appropriately determined and applied treatment may lead to less therapeutics being required for a patient or may lead to avoiding or delaying a biopsy, a resection, or other invasive procedure. When regions of cancerous tissue, including BCa are more quickly and more accurately classified, patients with poorer prognoses may receive a higher proportion of scarce resources (e.g., therapeutics, physician time and attention, hospital beds) while those with better prognoses may be spared unnecessary treatment, which in turn spares unnecessary expenditures and resource consumption. Example methods and apparatus may thus have the real-world, quantifiable effect of improving patient outcomes or reducing expenditures.

While FIG. 1 illustrates various actions occurring in serial, it is to be appreciated that various actions illustrated in FIG. 1 could occur substantially in parallel. By way of illustration, a first process could generate a tile sampling selection, a second process could provide the sampling subset to an automated classifier, and a third process could construct a probability map. While three processes are described, it is to be appreciated that a greater or lesser number of processes could be employed and that lightweight processes, regular processes, threads, and other approaches could be employed.

Figure 2:
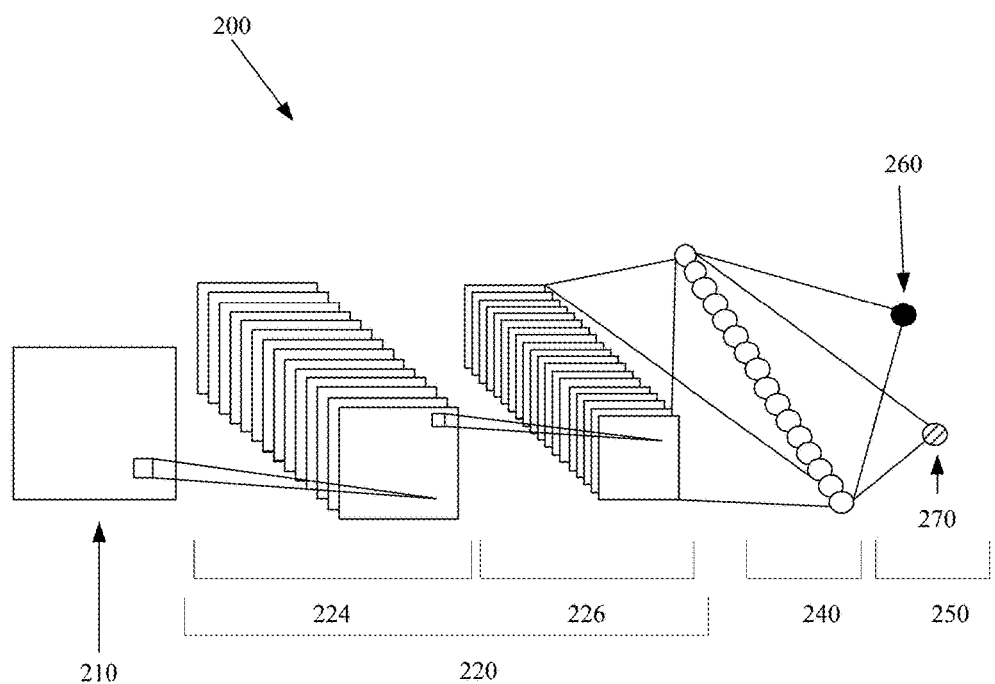
FIG. 2 illustrates an example convolutional neural network (CNN) architecture.

FIG. 2 illustrates in greater detail an example CNN architecture 200 that may be implemented with example methods and apparatus described herein. CNN architecture 200 may be used to distinguish between invasive tissue and non-invasive tissue, including invasive BCa and non-invasive BCa, represented in an image 210. Image 210 may be, for example, a digitized WSI of a region of tissue demonstrating cancerous pathology. In one embodiment, CNN architecture 200 is a two-layer CNN with 256 neurons or units in a first layer 220 and 256 neurons or units in a fully connected layer 240. CNN architecture 200 may thus be described as a (CS256-FC-256) architecture. First layer 220 comprises a convolutional layer 224 followed by a pooling layer 226. Convolutional layer 224 applies a 2D convolution of the input image 210 with a kernel of eight pixels by eight pixels to produce a feature map. Pooling layer 226, which may also be referred to as a subsampling layer, applies a spatial L2-pooling function without overlapping, using a pooling kernel of two pixels by two pixels, to a feature map obtained from convolutional layer 224. The output of pooling layer 226 is fed to fully connected layer 240. Fully connected layer 240 outputs to a final classification layer 250. Final classification layer 250 is a softmax classifier comprising an invasive tissue output 260 and a non-invasive tissue output 270. Invasive tissue output 260 and non-invasive tissue output 270 are activated by a logistic regression function. In another embodiment, CNN architecture 200 may be a different CNN architecture, including a (CS16-CS32-FC-128) architecture, or a (CS16-CS16-CS16-CS16-FC128) architecture. In another embodiment, the final classification layer 250 may employ other, different types of classifier.

Figure 3:
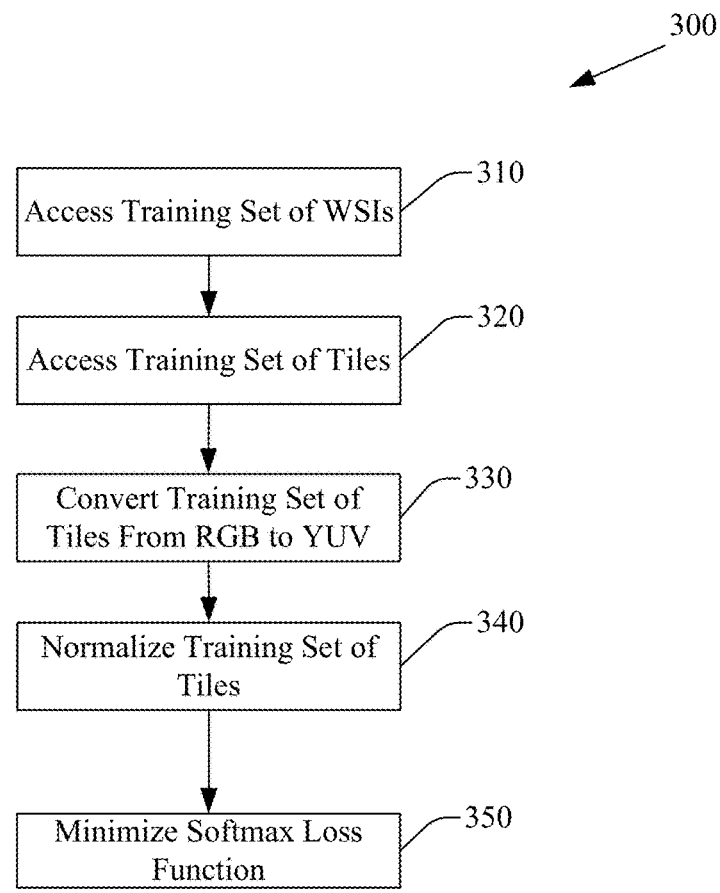
FIG. 3 illustrates an example method of training a CNN.

In one embodiment, example methods and apparatus described herein may train an automated classifier. FIG. 3 illustrates an example method 300 for training an automated classifier suitable for implementation with methods and apparatus described herein. Method 300 includes, at 310, accessing a set of digitized WSIs of tissue demonstrating invasive pathology and non-invasive pathology. The set of digitized WSIs may be annotated by an expert pathologist. A member of the set of digitized WSIs includes a set of tiles. A member of the set of digitized WSIs may be an RGB color model WSI. Accessing the set of digitized WSIs may also include accessing another type of medical image of a region of tissue demonstrating a different, non-cancerous pathology. Accessing the set of digitized WSIs may include retrieving electronic data from a computer memory, receiving a computer file over a computer network, or other computer or electronic based action.

Method 300 also includes, at 320, accessing a training set of tiles. The training set of tiles is accessed from the set of digitized WSIs. The training set includes a tile sampled from a region of invasive BCa tissue, and a tile sampled from a region of non-invasive tissue. Members of the training set may be sampled from a WSI using regular sampling. A member of the training set may also be considered invasive if a threshold proportion of the member of the training set's area overlaps with a region annotated by an expert pathologist as invasive.

Method 300 also includes, at 330, converting the training set of tiles from RBG color space to YUV color space. Method 300 also includes, at 340, normalizing the training set of tiles. Normalizing the training set of tiles includes normalizing the training set of tiles to a mean of zero and a variance of one. Converting the training set of tiles from RGB color space to YUV color space, and normalizing the training set of tiles, facilitates the decolorization and accentuation of differences between input image tiles, independent of the color variability. Example methods and apparatus thus improve on conventional approaches by facilitating the acceleration of the gradient-based learning process when training the CNN classifier.

Method 300 further includes, at 350 minimizing a softmax loss function. Example methods and apparatus may minimize the softmax loss function using a stochastic gradient descent. Minimizing the softmax loss function may include searching for a weight vector that minimizes the softmax loss function. In other embodiments, other types of loss function may be minimized using other approaches.

In one example, a method may be implemented as computer executable instructions. Thus, in one example, a computer-readable storage medium may store computer executable instructions that if executed by a machine (e.g., computer) cause the machine to perform methods described or claimed herein including method 100, method 300, method 400, and method 600. While executable instructions associated with the listed methods are described as being stored on a non-transitory computer-readable storage medium, it is to be appreciated that executable instructions associated with other example methods described or claimed herein may also be stored on a non-transitory computer-readable storage medium. In different embodiments the example methods described herein may be triggered in different ways. In one embodiment, a method may be triggered manually by a user. In another example, a method may be triggered automatically.

Figure 5:
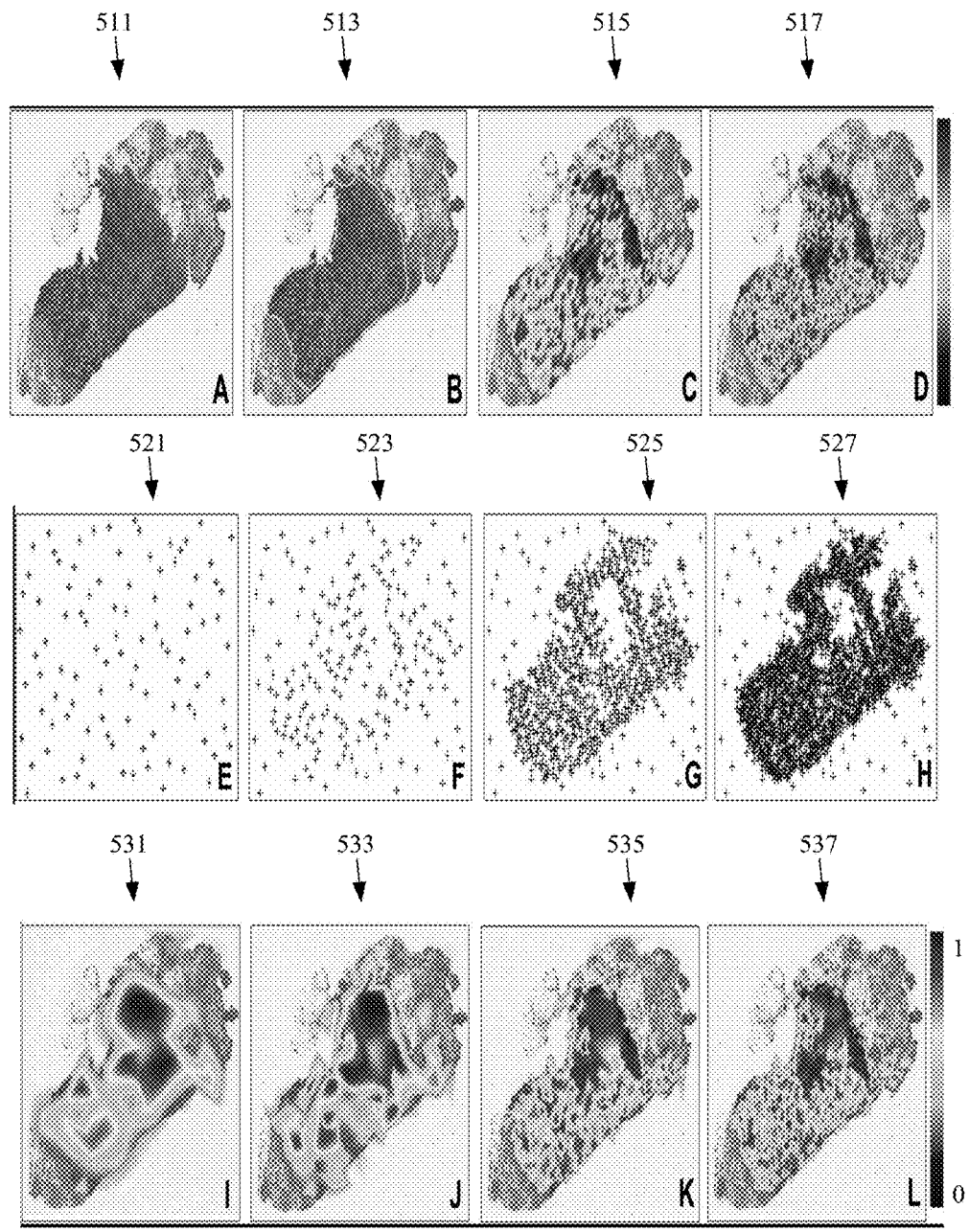
FIG. 5 illustrates sampling selections and invasive BCa probability maps produced for a sample WSI.

FIG. 5 illustrates invasive BCa probability maps produced for a sample WSI using a (CS256-FC256) two-layer CNN. Recall that a probability map as described herein represents the probability that a region of tissue represented in a WSI contains invasive or non-invasive tissue. FIG. 5 presents iterations of regular and dense sampling approaches of a region of tissue demonstrating BCa in a digitized WSI produced by example methods and apparatus in comparison with conventional approaches. FIG. 5 illustrates a test WSI 511 of a region of tissue demonstrating BCa. FIG. 5 also illustrates a corresponding ground truth annotation 513 of test WSI 511 as prepared by an expert pathologist. Probability map 515 is generated by conventional approaches from the test WSI 511 using regular sampling with a step size equal to the patch or tile size. In this example, the step size represented in probability map 515 is 50 pixels. While conventional approaches may be able to generate probability map 515 in a clinically relevant time frame of, for example, 31 seconds, probability map 515 is too coarse and imprecise to provide useful information to a clinician. A probability map 517 generated from the test WSI 511 by conventional approaches using regular dense sampling with a step size equal to one is also illustrated. Probability map 517, while more detailed and specific than probability map 515, takes approximately 22 hours to generate, and is also therefore not clinically feasible. Elements 521, 523, 525, and 527 illustrate points sampled from WSI 511 at iterations 1, 2, 8, and 20 respectively of example methods described herein, using gradient-based QMC sampling with a Halton sequence as described herein. Tile samples extracted after one iteration are illustrated at 521. Tile samples after two iterations are illustrated at 523. Tile samples extracted after eight iterations are illustrated at 525. Tile samples extracted after 20 iterations are illustrated at 527. Corresponding probability maps are illustrated by probability map 531, probability map 533, probability map 535, and probability map 537. Probability map 531 corresponds with the samples extracted after one iteration illustrated at 521. Probability map 533 corresponds with the samples illustrated at 523. Probability map 535 corresponds with the samples illustrated at 525, and probability map 537 corresponds with the samples extracted after 20 iterations illustrated at 527. As illustrated in FIG. 5, example methods and apparatus using a (CS256-FC256) two-layer CNN achieve an invasive BCa detection performance equivalent to or better than dense regular sampling in less than one minute, compared to the approximately 24 hour run time required by regular dense sampling using the same (CS256-FC256) two-layer CNN.

Figure 6:
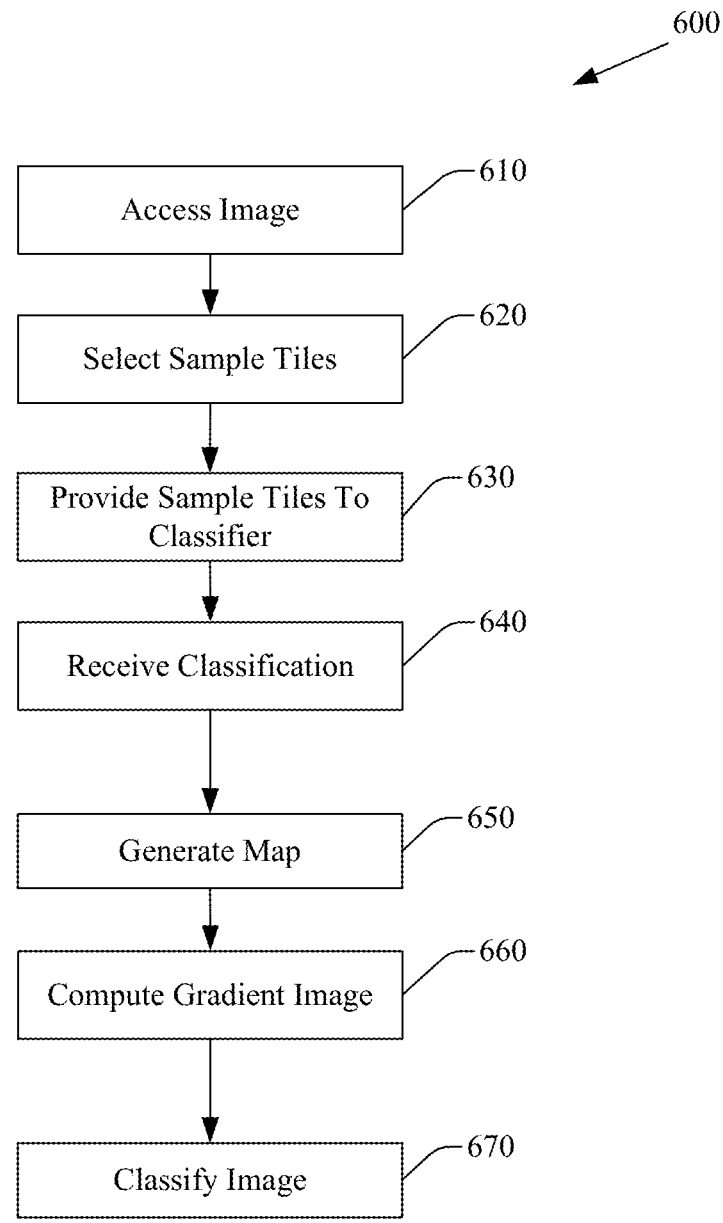
FIG. 6 illustrates an example method for classifying a region of tissue.

FIG. 6 illustrates an example method 600 for identifying and localizing invasive tissue in a radiological image of a region of tissue. Method 600 includes, at 610, accessing a radiological image of a region of tissue demonstrating invasive pathology. The radiological image may be a digitized WSI of a hematoxylin and eosin (H&E) stained histopathology slide of a region of tissue demonstrating cancerous pathology. The radiological image comprises a set of tiles. Accessing the radiological image may include retrieving electronic data from a computer memory, receiving a computer file over a computer network, or other computer or electronic based action.

Method 600 also includes, at 620, selecting a sample set of tiles from the set of tiles using a gradient-based quasi-Monte Carlo (QMC) sampling approach. In one embodiment, the gradient-based QMC sampling approach uses a Sobol sequence or a Halton sequence. In another embodiment, other gradient-based random sampling approaches may be employed.

Method 600 also includes, at 630, providing the sample set of tiles to an automated classifier. In one embodiment, the automated classifier is a two-layer CNN comprising a (CS256-FC256) architecture. The automated classifier classifies a member of the sample set of tiles as invasive or non-invasive. The automated classifier may determine a probability that a member of the sample set of tiles is invasive or non-invasive by minimizing a loss function. The loss function may be a softmax loss function. In another embodiment, other, different types of automated classifiers may be used.

Method 600 also includes, at 640, receiving, from the automated classifier, a classification of the sample set of tiles. The classification indicates the probability that a tile represents invasive tissue. Receiving the classification may include retrieving electronic data from a computer memory, receiving a computer file over a computer network, or other computer or electronic based action.

Method 600 also includes, at 650, generating an invasiveness probability map based, at least in part, on the classification. In one embodiment, method 600 generates at 650 the invasiveness map by cubically interpolating the classification of the sample set of tiles to the remaining tiles, or to a subset of the remaining tiles of the WSI from which the sample set of tiles was selected. In another embodiment, method 600 may extend the probability estimation to other tiles or pixels in the WSI using other approaches.

Method 600 also includes, at 660, computing a gradient image based, at least in part, on the invasiveness probability map. The gradient image expresses directional changes in the X and Y directions of the invasiveness probability map. Method 600 may update the sampling selection based, at least in part, on the gradient image. Method 600 may update the sampling selection using an iterative gradient-based QMC sampling approach with a Halton sequence or a Sobol sequence. In another embodiment, method 600 may update the sampling selection using other, different approaches.

Method 600 also includes, at 670, providing an invasiveness classification and localization for the WSI based on the invasiveness probability map and the gradient image. The invasiveness classification and localization classifies the region of tissue as invasive or non-invasive, and localizes sub-regions within the region of tissue as invasive or non-invasive. The invasiveness classification and localization for the WSI may be used by a decision support tool or a CADx system to facilitate identification and localization of invasive tissue.

Method 600 may repeat steps 620, 630, 640, 650, and 660 until a termination condition is met. The termination condition may be a maximum number of iterations, a steady state condition, a time limit, a minimum epsilon value for the average magnitude gradient of the gradient image, or a minimum approximation error between the current invasiveness probability map and a previous invasiveness probability map.

Figure 7:
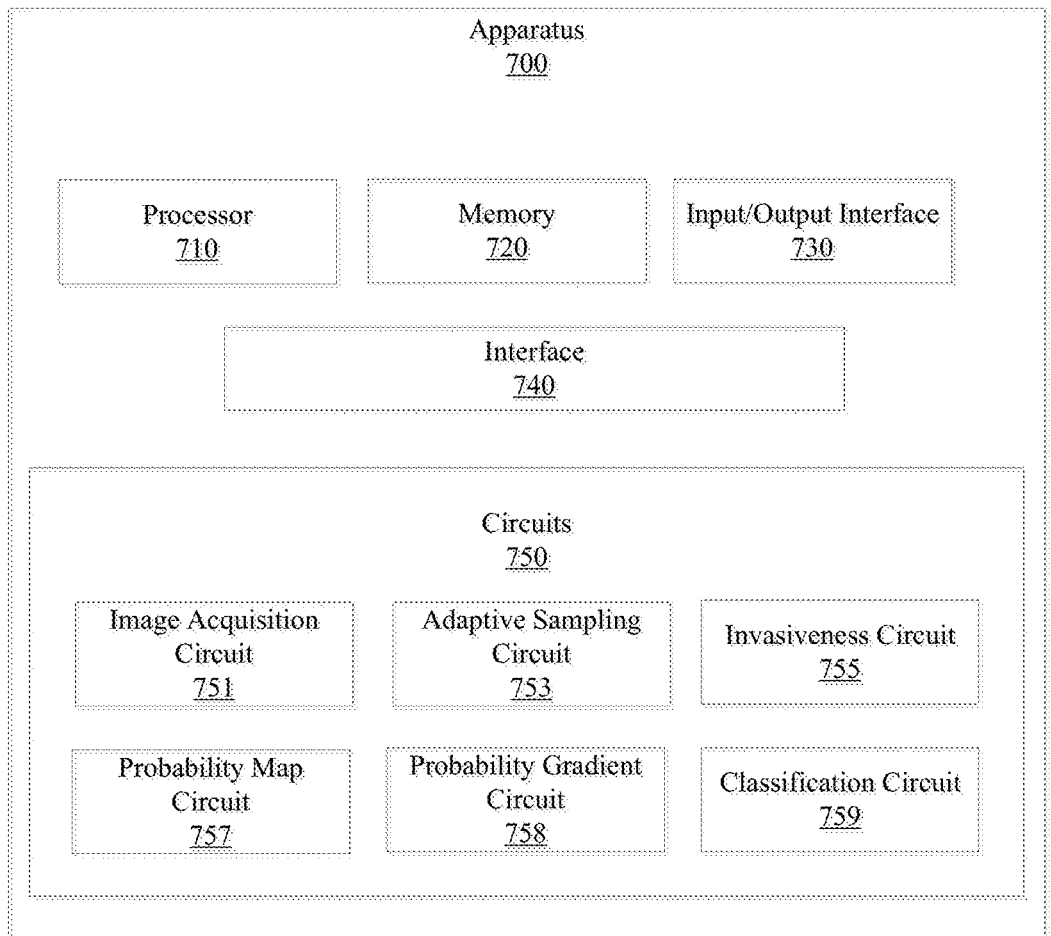
FIG. 7 illustrates an example apparatus that classifies a region of tissue in an image.

FIG. 7 illustrates an example apparatus 700 for classifying a region of tissue in an image. Apparatus 700 includes a processor 710, a memory 720 that stores a digitized WSI or a medical image, an input/output (I/O) interface 730, a set of circuits 750, and an interface 740 that connects the processor 710, the memory 720, the I/O interface 730, and the set of circuits 750. The set of circuits 750 includes an image acquisition circuit 751, an adaptive sampling circuit 753, an invasiveness circuit 755, a probability map circuit 757 that generates an invasiveness probability map, a probability gradient circuit 758 that generates a gradient image, and a classification circuit 759. In one embodiment, the functionality associated with the set of circuits 750 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of circuits 750 are implemented as ASICs or SOCs.

Image acquisition circuit 751 acquires an image of a region of tissue demonstrating cancerous pathology, where the image comprises a set of tiles. In one embodiment, the image is a digitized WSI of an H&E stained histological slide of a region of tissue demonstrating estrogen receptor-positive (ER+) breast cancer. In another embodiment, the image may be a different type of image, or may be of a region of tissue demonstrating another, different type of invasive pathology. Acquiring the image may include retrieving electronic data from a computer memory, receiving a computer file over a computer network, or other computer or electronic based action.

Adaptive sampling circuit 753 selects a subset of tiles from the image using an iterative quasi-Monte Carlo sampling approach. In one embodiment, adaptive sampling circuit 753 selects an updated subset of tiles from the image based on the gradient image by generating a set of 2N sample tiles using an iterative random sampling approach or an iterative QMC sampling approach. A member of the set of 2N sample tiles has a gradient magnitude. Adaptive sampling circuit 753 ranks the set of 2N sample tiles according to a gradient magnitude associated with a member of the set of 2N sample tiles. Adaptive sampling circuit 753 selects the top N sample tiles from the set of 2N sample tiles according to the gradient magnitude. Adaptive sampling circuit 753 may iteratively add sample points over the course of multiple iterations without discarding sample points already generated.

Invasiveness circuit 755 determines a probability of a presence of invasive pathology in a member of the subset of tiles using a two-layer convolutional neural network (CNN). In one embodiment, invasiveness circuit 755 determines the probability using a two-layer CNN classifier that employs a (CS256-FC256) architecture. The two-layer CNN classifier includes a classification layer that outputs a non-invasive output or an invasive output, activated by a logistic regression function. The classification layer may be a softmax classifier that minimizes a softmax loss function. In another embodiment, other CNN architectures may be employed.

Probability map circuit 757 generates an invasiveness probability map based, at least in part, on the probability. Probability map circuit 757 cubically interpolates the probability to extend the probability from the subset of tiles to other tiles that are not members of the subset of tiles in the image. For example, in one embodiment, probability map circuit 757 may cubically interpolate the probability from the subset of tiles to all the remaining tiles in the WSI. In another embodiment, probability map circuit 757 may cubically interpolate the probability from the subset of tiles to less than all the remaining tiles in the WSI, or may cubically interpolate the probability from less than all of the tiles in the subset of tiles the remaining tiles in the WSI. In another embodiment, probability map circuit 757 may extend the estimation of the probability from the subset of tiles to other tiles in the WSI using other techniques.

Probability gradient circuit 758 generates a gradient image based, at least in part, on the probability or the invasiveness probability map. The gradient image identifies the directional changes of the probability map in the X direction and the directional changes of the probability map in the Y direction. Probability gradient circuit 758 also computes a gradient magnitude image that facilitates identifying regions in the image with high or low variations among tissue types. Areas in the gradient magnitude image with high values indicate spatial regions of the probability map that have large differences in probability values, while areas in the gradient magnitude map with low values indicate local spatial regions of the probability map that have similar values. Computing the probability gradient and generating the gradient image facilitates more intelligent spatial sampling of points with a denser sampling directed at high gradient magnitude regions, while fewer samples are selected from homogeneous regions. Thus, adaptive sampling circuit 753 may, by selecting the N sample tiles that have higher gradient magnitudes, improve on conventional approaches by directing more computational resources to analyze regions within the WSI that are more likely to indicate boundary regions between invasive and non-invasive tissue, and by directing less computational resources to analyze regions within the WSI that are more likely to be homogeneous.

Classification circuit 759 classifies the region of tissue based, at least in part, on the probability map. In one embodiment, classification circuit 759 classifies the region of tissue as invasive BCa or non-invasive BCa with an accuracy of at least 0.9018 AUC. Classification circuit 759 achieves a Dice coefficient when classifying the region of tissue of between 0.7 and 0.9 with a median Dice coefficient of 0.8228. The Dice coefficient may be expressed as $$Dice = \frac{2|P \cap G|}{|P| + |G|}$$

where P corresponds to the region predicted to be invasive by example methods and apparatus, while G is a ground truth binary mask obtained by expert pathologist annotation. Compared to conventional approaches that are unstable and achieve clinically useful results only in the threshold probability interval of 0.35 to 0.45, example methods and apparatus are stable and achieve Dice coefficients of 0.7 or greater over a wider threshold probability interval of at least 0.1 to 0.6.

In one embodiment of apparatus 700, adaptive sampling circuit 753 may determine that apparatus 700 may terminate analysis of the WSI. Adaptive sampling circuit 753 may determine that apparatus 700 may terminate analysis of the WSI by determining that a termination condition has been satisfied. In one example, the termination condition may be a maximum number of iterations, a maximum amount of time spent analyzing the image, or may be a steady state condition. In one embodiment, the termination condition is a minimum epsilon value for the average magnitude gradient of the gradient image, or a minimum approximation error between a current invasiveness probability map and a previous invasiveness probability map. The termination condition may be user controlled.

In one embodiment of apparatus 700, the set of circuits 750 also includes a display circuit. The display circuit may control a CADx system to display the classification, the probability gradient, or the probability map, on a computer monitor, a smartphone display, a tablet display, or other displays. Displaying the classification, the probability gradient, or the probability map may also include printing the classification, the probability gradient, or the probability map. The display circuit may also control the CADx system to display an image of the region of tissue demonstrating invasive or non-invasive pathology. The image of the region of tissue demonstrating invasive or non-invasive pathology may include a delineated or segmented representation of the region of tissue. By displaying the classification, the probability gradient, the probability map, or the image of invasive or non-invasive pathology, example apparatus provide a timely and intuitive way for a human pathologist to more accurately classify pathologies demonstrated by a patient, thus improving on conventional approaches to detecting disease invasiveness.

Figure 8:
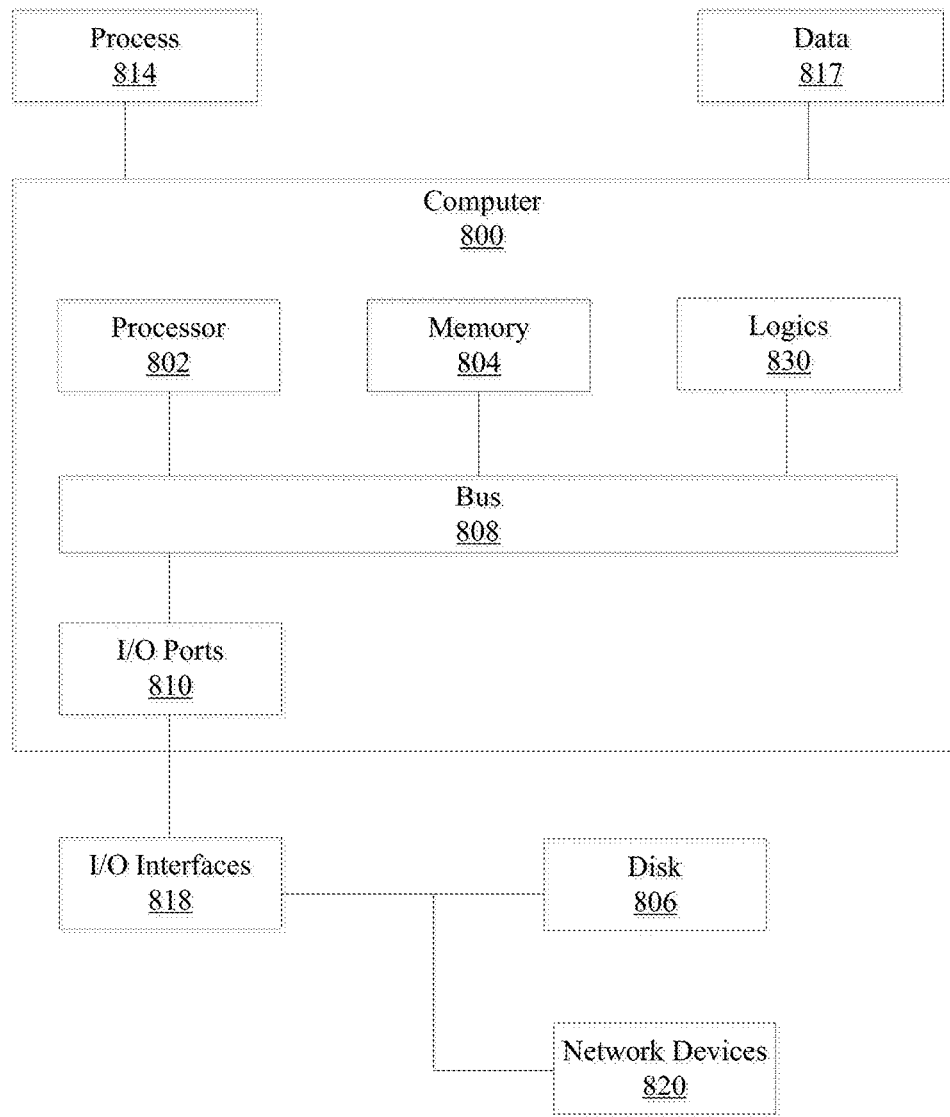
FIG. 8 illustrates an example computer in which example methods and apparatus may operate.

FIG. 8 illustrates an example computer 800 in which example methods illustrated herein can operate and in which example circuits or logics may be implemented. In different examples, computer 800 may be part of a WSI scanner system, a CT system or MRI system, may be operably connectable to a WSI scanner system, a CT system or MRI system, or may be part of a decision support system or a CADx system.

Computer 800 includes a processor 802, a memory 804, and input/output ports 810 operably connected by a bus 808. In one example, computer 800 may include a set of logics 830 that perform a method of characterizing a region of tissue. Thus, the set of logics 830, whether implemented in computer 800 as hardware, firmware, software, and/or a combination thereof may provide means (e.g., hardware, software) for characterizing a region of tissue. In different examples, the set of logics 830 may be permanently and/or removably attached to computer 800. In one embodiment, the functionality associated with the set of logics 830 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 830 are implemented as ASICs or SOCs.

Processor 802 can be a variety of various processors including dual microprocessor and other multi-processor architectures. Memory 804 can include volatile memory and/or non-volatile memory. A disk 806 may be operably connected to computer 800 via, for example, an input/output interface (e.g., card, device) 818 and an input/output port 810. Disk 806 may include, but is not limited to, devices like a magnetic disk drive, a tape drive, a Zip drive, a solid state device (SSD), a flash memory card, a shingled magnetic recording (SMR) device, or a memory stick. Furthermore, disk 806 may include optical drives like a CD-ROM or a digital video ROM drive (DVD ROM). Memory 804 can store processes 814 or data 817, for example. Disk 806 or memory 804 can store an operating system that controls and allocates resources of computer 800.

Bus 808 can be a single internal bus interconnect architecture or other bus or mesh architectures. While a single bus is illustrated, it is to be appreciated that computer 800 may communicate with various devices, logics, and peripherals using other busses that are not illustrated (e.g., PCIE, SATA, Infiniband, 1394, USB, Ethernet).

Computer 800 may interact with input/output devices via I/O interfaces 818 and input/output ports 810. Input/output devices can include, but are not limited to, digital whole slide scanners, a CT machine, an MRI system, an optical microscope, a keyboard, a microphone, a pointing and selection device, cameras, video cards, displays, disk 806, network devices 820, or other devices. Input/output ports 810 can include but are not limited to, serial ports, parallel ports, or USB ports.

Computer 800 may operate in a network environment and thus may be connected to network devices 820 via I/O interfaces 818 or I/O ports 810. Through the network devices 820, computer 800 may interact with a network. Through the network, computer 800 may be logically connected to remote computers. The networks with which computer 800 may interact include, but are not limited to, a local area network (LAN), a wide area network (WAN), or other networks.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a non-transitory medium that stores instructions or data. "Computer-readable storage medium" does not refer to propagated signals. A computer-readable storage medium may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage medium may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, a data storage device, and other media from which a computer, a processor or other electronic device can read.

"Circuit", as used herein, includes but is not limited to hardware, firmware, software in execution on a machine, or combinations of each to perform a function(s) or an action (s), or to cause a function or action from another circuit, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logics into one physical logic or circuit. Similarly, where a single logical circuit is described, it may be possible to distribute that single logic between multiple logics or circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage medium storing computer executable instructions that when executed by a computer control the computer to perform a method for detecting cancerous pathology in a region of tissue, the method comprising:

accessing an image of a region of tissue demonstrating cancerous pathology, where the image comprises a set of tiles;

generating a tile sampling selection, where the tile sampling selection defines a sampling subset of the set of tiles, where the number of tiles in the sampling subset is N, where N is less than the number of tiles in the set of tiles, N being an integer;

upon determining that a termination condition has not been met:
extracting the sampling subset from the image based on the tile sampling selection;
providing the sampling subset to an automated classifier;
receiving, from the automated classifier, a prediction probability based, at least in part, on the sampling subset, where the prediction probability indicates the probability of invasive pathology at a location in the image occupied by a tile;
constructing a probability map of the region of tissue based on the prediction probability or the sampling subset;
computing a gradient of the probability map; and
updating the tile sampling selection based on the gradient of the probability map;

upon determining that the termination condition has been met:
constructing a final probability map based, at least in part, on the probability map; and controlling a computer aided diagnosis (CADx) system to generate a classification of the region of tissue based, at least in part, on the final probability map.

2. The non-transitory computer-readable storage medium of claim 1, where the image of the region of tissue is a digitized whole slide image (WSI) of a region of tissue demonstrating estrogen receptor-positive (ER+) BCa.

3. The non-transitory computer-readable storage medium of claim 2, where the WSI is a red-green-blue (RGB) color model WSI, where the WSI has dimensions of 80,000 pixels by 80,000 pixels.

4. The non-transitory computer-readable storage medium of claim 3, where a tile has dimensions of 101 pixels by 101 pixels.

5. The non-transitory computer-readable storage medium of claim 1, where generating the tile sampling selection comprises:
selecting the sampling subset of the set of tiles using a regular sampling approach, a uniform random sampling approach, or a quasi-Monte Carlo sampling approach.

6. The non-transitory computer-readable storage medium of claim 5, where the quasi-Monte Carlo sampling approach employs a deterministic sequence.

7. The non-transitory computer-readable storage medium of claim 6, where the deterministic sequence has a low discrepancy.

8. The non-transitory computer-readable storage medium of claim 7, where the deterministic sequence measures a uniformity of a distribution of finite point sets.

9. The non-transitory computer-readable storage medium of claim 8, where the deterministic sequence is a Sobol sequence or a Halton sequence.

10. The non-transitory computer-readable storage medium of claim 1, where the termination condition comprises a number of iterations, a steady state condition, a processing time limit, a minimum epsilon value for an average magnitude gradient of the probability map, or a minimum approximation error between a first probability map and a second, different probability map.

11. The non-transitory computer-readable storage medium of claim 10, where the number of iterations is twenty.

12. The non-transitory computer-readable storage medium of claim 1, where the prediction probability represents the probability of invasive pathology at the location in the image occupied by a tile.

13. The non-transitory computer-readable storage medium of claim 12, where constructing the probability map based on the prediction probability and the set of tiles comprises cubically interpolating the prediction probability to a plurality of tiles in the image.

14. The non-transitory computer-readable storage medium of claim 13, where computing the gradient of the probability map comprises:
    calculating a gradient image based on an X direction gradient and a Y direction gradient, where the X direction gradient represents a directional change of the probability map in the X direction, and where the Y direction gradient represents a directional change of the probability map in the Y direction; and
    computing a gradient magnitude image based, at least in part, on the gradient image or the X direction gradient and the Y direction gradient.

15. The non-transitory computer-readable storage medium of claim 14, where updating the tile sampling selection based on the gradient of the probability map comprises:
    selecting 2N sample tiles from the set of tiles using a quasi-Monte Carlo sampling approach or a random sampling approach; and
    generating an updated sampling selection by determining the N tiles that have the highest gradient magnitude from the 2N sample tiles, where the updated sampling selection comprises the N tiles that have the highest gradient magnitude from the 2N sample tiles.

16. The non-transitory computer-readable storage medium of claim 15, where determining the N tiles from the 2N sample tiles that have the highest gradient magnitude comprises:
    generating a ranked set of sample tiles based, at least in part, on the gradient magnitude image; and
    selecting the N highest ranked sample tiles from the ranked set of sample tiles.

17. The non-transitory computer-readable storage medium of claim 1, where the automated classifier is a 2-layer convolutional neural network (CNN) comprising:
    a first layer comprising a 256 unit convolutional layer and a 256 unit pooling layer;
    a second layer comprising a 256 unit fully-connected layer; and
    a classification layer, where the classification layer is a softmax classifier, where the classification layer produces a first output activated by a logistic regression function and a second output activated by the logistic regression function.

18. The non-transitory computer-readable storage medium of claim 17, where the convolutional layer generates a feature map by applying a 2 dimensional (2D) convolution of an input image with an 8 pixel by 8 pixel kernel.

19. The non-transitory computer-readable storage medium of claim 18, where the pooling layer applies a spatial L2 pooling function without overlapping to the feature map, where the pooling layer applies a 2 pixel by 2 pixel pooling kernel to the feature map.

20. The non-transitory computer-readable storage medium of claim 1, the method further comprising training the automated classifier.

21. The non-transitory computer-readable storage medium of claim 20, where training the automated classifier comprises training a CNN model by:
    accessing a set of digital WSIs of tissue demonstrating invasive pathology and non-invasive pathology, where a member of the set of digital WSIs comprises a set of tiles, where a member of the set of digital WSIs is an RGB color model WSI;
    accessing a training set of tiles, where the training set includes a tile sampled from a region of invasive BCa tissue, and a tile sampled from a region of non-invasive tissue;
    converting the training set of tiles from RGB color space to YUV color space;
    normalizing the training set of tiles to a mean of zero and a variance of one; and
    minimizing a softmax loss function using a stochastic gradient descent.

22. A non-transitory computer-readable storage medium storing computer executable instructions that when executed by a computer control the computer to perform a method, the method comprising:
    accessing a radiological image of a region of tissue demonstrating invasive pathology, where the radiological image comprises a set of tiles;
    selecting a sample set of tiles from the set of tiles using a gradient-based quasi-Monte Carlo sampling approach;
    providing the sample set of tiles to an automated classifier;
    receiving, from the automated classifier, a classification of the sample set of tiles;
    generating an invasiveness probability map based, at least in part, on the classification;
    computing a gradient image based, at least in part, on the invasiveness probability map; and
    providing an invasiveness classification and localization based on the invasiveness probability map and the gradient image.

23. An apparatus for detecting cancerous pathology in a region of tissue, comprising:
    a processor;
    a memory;
    an input/output interface;
    a set of circuits; and
    an interface to connect the processor, the memory, the input/output interface and the set of circuits, where the set of circuits includes:
        an image acquisition circuit that acquires an image of a region of tissue demonstrating cancerous pathology, where the image comprises a set of tiles;
        an adaptive sampling circuit that selects a sampling subset of tiles from the image where the sampling subset of tiles comprises N tiles, where N is less that the number of tiles in the set of tiles, N being an integer;
        an invasiveness circuit that determines a probability of a presence of invasive pathology in a member of the sampling subset of tiles;
        a probability map circuit that generates an invasiveness probability map based, at least in part, on the probability;

a probability gradient circuit that generates a gradient image based, at least in part, on the invasiveness probability map, where the gradient image identifies directional changes of the invasiveness probability map; and a classification circuit that classifies the region of tissue based, at least in part, on the probability map.

24. The apparatus of claim 23, where the adaptive sampling circuit selects the sampling subset of tiles using an iterative quasi-Monte Carlo (QMC) Sobol sequence sampling approach or an iterative QMC Halton sequence sampling approach.

25. The apparatus of claim 23, where the adaptive sampling circuit selects the sampling subset of tiles using a uniform random sampling approach, or a gradient-based random sampling approach.

26. The apparatus of claim 23, where the adaptive sampling circuit selects an updated subset of tiles from the image based on the gradient image, where the adaptive sampling circuit generates a set of 2N sample tiles using an iterative random sampling approach or an iterative quasi-Monte Carlo (QMC) sampling approach, where a member of the set of 2N sample tiles has a gradient magnitude, where the adaptive sampling circuit ranks the set of 2N sample tiles according to a gradient magnitude associated with a member of the set of 2N sample tiles, and where the adaptive sampling circuit selects the N sample tiles that have the highest gradient magnitudes from the set of 2N sample tiles according to the gradient magnitude.

27. The apparatus of claim 23, where the invasiveness circuit determines the probability using a two-layer convolutional neural network (CNN) classifier trained using a stochastic gradient descent approach.

28. The apparatus of claim 27, where the CNN classifier employs a (CS256-FC256) architecture comprising a softmax classification layer.

29. The apparatus of claim 23, where the probability gradient circuit generates the gradient image based on a gradient in the X direction and a gradient in the Y direction, where the gradient in the X direction identifies a change in the probability in the X direction, and the gradient in the Y direction identifies a change in the probability in the Y direction, where a high gradient magnitude corresponds to a heterogeneous spatial distribution of invasive tissue or non-invasive tissue, and where a low gradient magnitude corresponds with a homogeneous distribution of invasive tissue or non-invasive tissue.

30. The apparatus of claim 23, where the probability map circuit generates the invasiveness probability map by extending the probability of the presence of invasive pathology in a member of the subset of tiles to member of the set of tiles that is not a member of the subset of tiles using cubic interpolation.

31. The apparatus of claim 23, where the image is a digitized whole slide image (WSI) of a region of tissue demonstrating estrogen receptor-positive (ER+) BCa.

* * * * *